(12) United States Patent
Tsang et al.

(10) Patent No.: US 6,966,692 B2
(45) Date of Patent: Nov. 22, 2005

(54) CLOUD POINT MONITORING DEVICE

(75) Inventors: Charles Y. Tsang, Vancouver (CA); Gordon S. Y. Chiu, Richmond (CA)

(73) Assignee: Phase Technology, Richmond (CA)

( * ) Notice: Subject to any disclaimer, the term of this patent is extended or adjusted under 35 U.S.C. 154(b) by 0 days.

(21) Appl. No.: 10/711,133

(22) Filed: Aug. 26, 2004

(65) Prior Publication Data

US 2005/0053116 A1  Mar. 10, 2005

Related U.S. Application Data

(62) Division of application No. 10/191,085, filed on Jul. 9, 2002, now Pat. No. 6,827,484.

(51) Int. Cl.[7] .............................................. G01N 25/04
(52) U.S. Cl. ........................ 374/20; 374/144; 374/45; 73/64.43
(58) Field of Search ............................ 374/16–20, 25, 374/45, 144; 73/64.43, 61.62

(56) References Cited

U.S. PATENT DOCUMENTS

| | | | | |
|---|---|---|---|---|
| 3,187,557 A | * | 6/1965 | Holbourne .................... | 374/19 |
| 3,527,082 A | * | 9/1970 | Pruvot et al. .................. | 374/17 |
| 4,519,717 A | * | 5/1985 | Jones et al. .................... | 374/17 |
| 4,570,069 A | * | 2/1986 | Gager .......................... | 250/343 |
| 4,760,538 A | * | 7/1988 | Bock et al. ................... | 702/136 |
| 4,804,274 A | * | 2/1989 | Green .......................... | 374/17 |
| 4,971,451 A | * | 11/1990 | Hori et al. .................... | 374/16 |
| 5,007,733 A | * | 4/1991 | Laurent et al. ............... | 356/70 |
| 5,088,833 A | * | 2/1992 | Tsang et al. .................. | 374/17 |
| 5,651,614 A | * | 7/1997 | Juneau ......................... | 374/17 |
| 5,708,196 A | * | 1/1998 | Tolvanen et al. ........... | 73/53.05 |
| 5,739,916 A | * | 4/1998 | Englehaupt ................. | 356/414 |
| 5,758,968 A | * | 6/1998 | Diebold ....................... | 374/17 |
| 6,679,226 B2 | * | 1/2004 | Burke et al. ................. | 123/509 |
| 6,712,503 B2 | * | 3/2004 | Lin et al. ..................... | 374/45 |
| 6,817,754 B2 | * | 11/2004 | Tsang et al. .................. | 374/20 |
| 6,827,484 B2 | * | 12/2004 | Tsang et al. .................. | 374/20 |
| 6,827,842 B2 | * | 12/2004 | Beasley et al. .............. | 208/27 |
| 2003/0140715 A1 | * | 7/2003 | Burke et al. ............. | 73/863.84 |

FOREIGN PATENT DOCUMENTS

| | | | | |
|---|---|---|---|---|
| GB | 1575819 A | * | 11/1980 | ......... G01N 25/04 |
| GB | 2202941 A | * | 10/1988 | ......... G01N 25/04 |

* cited by examiner

*Primary Examiner*—Gail Verbitsky
*Assistant Examiner*—Stanley J. Pruchnic, Jr.
(74) *Attorney, Agent, or Firm*—John J. Elnitski, Jr.

(57) ABSTRACT

A cloud point monitoring device which includes thermal conductive surface, cooler, temperature sensor, detection volume, detection wall unit, fiber optic cables for transmitting light, lighter emitter, light detector, and a data acquisition and control unit. The cloud point monitoring device provides an instrument to accurately measure the cloud point of diesel fuel indicate the approximate level of crystallization in diesel fuel that has been chilled beyond its cloud point and indicate the approximate energy content of diesel fuel. The cloud point monitoring device design allows it to be made small enough to be mounted in a fuel system of a vehicle.

36 Claims, 23 Drawing Sheets

CLOUD POINT MONITORING DEVICE

DESCRIPTION

The present invention generally relates to monitoring cloud point temperature, crystallization and energy content of diesel fuel in cold temperature conditions. More specifically, the present invention relates to a device for monitoring cloud point temperature of diesel fuel onboard vehicles in cold temperature conditions.

Diesel is the most common form of fuel for heavy-duty trucks of the shipping industry worldwide. Due to its high-energy content and thus better fuel economy, diesel is also widely used by passenger cars in many countries. Especially in Europe, where more than twenty percent (20%) of passenger vehicles are powered by diesel. Diesel engines become inoperable when the fuel temperature falls below the cloud point of the fuel, due to wax crystals forming in the fuel and plugging the fuel tank filter. The formation of wax crystals in the diesel fuel is commonly referred to as gelling. Blending, cold-flow additives, fuel heaters and engine idling are all ways to mitigate the formation of wax crystals in diesel fuel, but these methods are all associated with important drawbacks and costs.

Blending is typically done in petroleum refineries, when cold weather is anticipated. A lighter fuel such as kerosene/jet fuel (commonly called No. 1 diesel in the U.S.) is blended into the regular diesel (No. 2 diesel in the U.S.) to lower the cloud point of the latter. However, blending is costly to the refineries, because kerosene/jet fuel commands a significantly higher market price than diesel fuel. Not only does the blended diesel cost more to produce, it also has lower energy content and poorer lubricity that decreases fuel economy and increases maintenance for the diesel vehicles. Fuel and maintenance are the main operating cost factors for the shipping industry. Moreover, blended diesel fuel supplied by one refinery cannot always address the cloud point needs of a large geographical region, where ambient temperature can vary significantly from one location to another. Nor does it always address the needs of the shipping industry, where trucks travel long distances. Consequently, it is common practice for many truck fleets, bulk fuel suppliers and individual truckers to perform their own blending of No. 1 and No. 2 diesels to meet the needs of their routes. Unfortunately, due to the lack of cloud point information, blending is often performed with little guidance other than past experience or guessing. Rough blending ratios of No. 1 and No. 2 diesels such as 1:1 or 1:2 are used, frequently without the knowledge of the cloud points of the diesel fuels that are being blended. Furthermore, without a cloud point analyzer, the final cloud point of the blended mixture cannot be verified. Over-dosing with No. 1 diesel is costly; while under-dosing could still render the vehicle inoperable in cold days. It should also be noted that fuel blending is often messy, cumbersome, and prone to inadvertent spillage. Fleet managers often instruct truck drivers to carry small quantities of fuel, such as fifty (50) gallons at a time during a long-haul route in cold weather, as compared to the typical one-hundred and twenty-five (125) gallons that can normally be carried. Such frequent stoppage for fuel greatly increases travel time; however, it does provide seasonably adjusted fuel along the route and thus lessen concern with gelling of the fuel.

Cloud point and related cold-flow properties of diesel fuels is information that is not traditionally provided to the consumer. For their peace of mind, many drivers often purchase costly cold additives with the intention of improving the cold-flow properties of their diesel fuel. However, without the knowledge of the fuel's cloud point, drivers actually do not know whether the diesel fuel requires any additive at all. There exists the possibility that the money spent on the additive is wasted, as the cloud point of the fuel may already be adequate for the journey. Even after the additive treatment, the drivers cannot check for any improvement offered by the additive, as there is no available means to validate improvement. It is usually very important with cold additives that the dispensing of the additive must precede any cold weather. This is because once the wax crystals begin to form, no amount of additive can reduce the wax crystals or salvage the loss of operability of the vehicle. The main problem with most cold additives available on the market is that they cannot significantly improve cloud point. They do not reduce the mass or amount of wax formation or the viscosity of the fuel. They can only claim the ability to reduce the dimensions of the individual wax crystals, if diesel fuel of compatible chemical composition is treated. In actuality, the number of wax crystals becomes larger because the total mass of crystallization cannot be changed by chemical additives. Whether or not this larger number of smaller wax crystals can pass through the fuel filter of the vehicle cannot be predicted, as there are multitudes of vehicle types and fuel-additive chemical systems. Finally, modification of the waxing properties of fuels using aftermarket fuel additives is generally not recommended by engine manufacturers and refineries, because of possible incompatibility with other additives already contained in the fuel.

Expensive fuel heaters can be added onto diesel vehicles to prevent gelling of the fuel. These fuel heaters are commonly located at the filter, fuel tank and delivery lines. The more common form of fuel heater creates heat using resistive elements powered by an electrical source of the vehicle. Alternatively, engine heat can be used through direct heat transfer to the fuel, or indirect transfer through a liquid medium such as engine coolant. The limitation is that all of the above heating methods are available only while the engine is running. These methods are therefore most useful when the vehicle is moving. They cannot help when the engine is stopped; for example, while the vehicle is parked overnight. In addition, warm fuel does not burn nearly as well as cold fuel and can result in poor fuel economy. Condensation often results in fuel tanks that go through this type of heat/cool temperature cycle. This can promote the growth of algae; therefore, drivers are often advised to run the heater only when needed. Some heavy-duty trucks are equipped with an automatic engine-starting-and-stopping feature based on the engine coolant temperature. This feature is not popular because many drivers do not want the engine running unattended. Moreover, engine coolant temperature is not indicative of fuel gelling and does not reliably serve as a control signal. Cloud point is a much more appropriate indicator for this operation.

Many heavy-duty diesel vehicles are left idling during cold winter nights to ensure that the fuel is kept above the cloud point by the heat generated from the engines and the heaters. The consumption of fuel/electricity is significant, not to mention the impact on the environment due to the idling. Impending EPA regulations are expected to severely curtail truck idling during cold weather. The idling is done because drivers have no knowledge of the cloud point of the fuel relative to the ambient temperature. If the cloud point is known in conjunction with the forecast temperature for the night, the drivers can make a more informed decision. This will significantly reduce the anxiety of the drivers, in addition to saving fuel and reducing pollution. The same concern with fuel gelling overnight also applies to passenger car owners, who may not have the means of parking their vehicles in heated or sheltered areas during cold nights.

Knowing the cloud point of the fuel in use, one can minimize and, in certain situations, completely avoid the drawbacks of the above-mentioned methods. In order to incorporate an analyzer into the fuel system of a diesel engine, there are important restrictions to be satisfied. These restrictions are often not considered or applicable for currently available cloud point instruments designed for use in laboratories or refinery process areas. For instance, as space is in short supply in a vehicle, the size and weight of the device becomes a key issue. Equally important is the manner in which the device is implemented, due to its proximity to a large amount of highly flammable material. There are additional requirements for on-board testing devices of diesel fuel in a vehicle. For example, the device must have a minimum demand on utilities such as gas, coolant and electricity, as they are either not conveniently available, or available only in limited quantity. Moreover, a land vehicle-mounted device must be rugged enough to withstand vibrations on the road and whereas a boat-mounted device must be able to withstand orientation change and vibrations in a rough sea. Most of the currently available instruments to test cloud point are large, use specialized gases and fluids, and are too delicate to mount on vehicles.

It is an object of the present invention to provide an onboard vehicle device for determining the cloud point of fuels used in a diesel engine to ensure that the engine is operated reliably and efficiently in cold temperatures.

It is another object of the present invention to provide an onboard vehicle device for determining cloud point to approximate wax buildup and energy content of fuels used in a diesel engine.

SUMMARY OF INVENTION

A cloud point monitoring device which includes thermal conductive surface, cooler, temperature sensor, detection volume, detection wall unit, fiber optic cables for transmitting light, lighter emitter, light detector, and a data acquisition and control unit. The cloud point monitoring device provides an instrument to accurately measure the cloud point of diesel fuel indicate the approximate level of crystallization in diesel fuel that has been chilled beyond its cloud point and indicate the approximate energy content of diesel fuel. The cloud point monitoring device design allows it to be made small enough to be mounted in a fuel system of a vehicle.

BRIEF DESCRIPTIONS OF THE DRAWINGS

DETAILED DESCRIPTION

The present invention is a cloud point monitoring device, as show in FIGS. 1–23. The cloud point monitoring device provides an instrument to accurately measure the cloud point of diesel fuel, indicate the approximate level of crystallization in diesel fuel that has been chilled beyond its cloud point and indicate the approximate energy content of diesel fuel. The cloud point monitoring device design allows it to be made small enough to be mounted in a fuel system of a vehicle. The cloud point monitoring device is preferably mounted on a diesel vehicle at a location where the physical state of the fuel is important to delivery of the fuel to the engine of the vehicle. Possible locations are the fuel line, fuel tank and fuel filter, which is why the cloud point monitoring device must be small. The cloud point monitoring device includes a means to detect the transition between liquid and solid phases, a means to cool the fuel to cause phase transition, and a means to process the data and relay the result to the user. The cloud point monitoring device is specifically useful for diesel engine vehicles that have a fuel system that is exposed to ambient temperatures. Some examples of such vehicles are cars, trucks, trains, tractors, mining equipment, snow-removal equipment, farming equipment, boats and ships. One could further expand the scope to include stationary facilities located in cold regions, such as radar stations and factories that rely on diesel powered equipment to drive electric generators.

Figure 1:
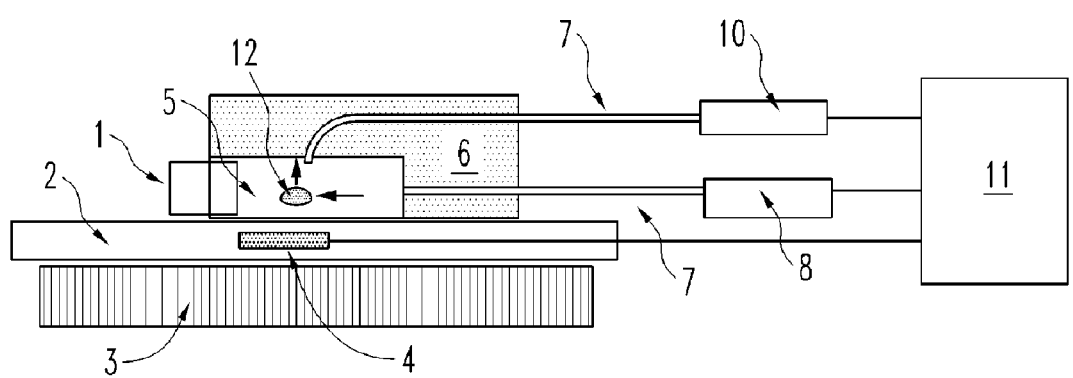
FIG. 1 is a schematic view of a configuration of the cloud point monitoring device according to present invention.

FIG. 1 shows the basic configuration of the cloud point monitoring device. The cloud point monitoring device of FIG. 1 includes a main volume 1, thermal conductive surface 2, cooler 3, temperature sensor 4, detection volume 5, detection wall unit 6, fiber optic cables 7 for transmitting light, lighter emitter 8, light detector 10, and a data acquisition and control unit 11. The cloud point monitoring device is located within a fuel flow to a diesel engine, whereby the flow of fuel fills the main volume 1 and hence fills the detection volume 5. The choice of the location of the cloud point monitoring device is contingent upon where the flow of fuel is considered critical to the successful operation of the diesel engine. This location may be inside the fuel tank or any portion of the fuel transfer line between the tank and engine, for example, near the fuel filter. To induce the formation and melting of wax crystals, the thermal conductive surface 2 is in contact with the cooler 3. The cooler 3 is a thermal device used to control the temperature of the thermal conductive surface 2 and hence the temperature of the fuel near the thermal conductive surface 2. By increasing the thermal transfer of cooling applied to the thermal conductive surface 2 the fuel is cooled and by decreasing the thermal transfer of cooling applied to the thermal conductive surface 2 the fuel is warmed. The temperature sensor 4 is embedded in the thermal conductive surface 2 to continuously monitor the temperature of the diesel fuel in close proximity of the thermal conductive surface 2. The thermal conductive surface 2, cooler 3 and temperature sensor 4 can also be combined into a single unit (not shown). Detection of the formation and melting of wax crystals takes place within the detection volume 5. The detection volume 5 is bounded at the top and one side by the detection wall unit 6 within the main volume 1, and at the bottom by the thermal conductive surface 2. The detection volume 5 is an area of fuel which can be thermally conditioned by the thermal conductive surface 2. Note that diesel fuel is free to flow into and out of the detection volume 5 via the remaining open three sides of the detection volume 5 that are not restricted by the detection wall unit 6.

The orientation of the thermal conductive surface 2 is preferably such that the wax crystals formed upon cooling are retained within the detection volume 5. In most situations, a horizontal position for the thermal conductive surface 2 is the preferred position, as the wax crystal will fall towards the thermal conductive surface 2 due to gravity. The thermal conductive surface 2, detection wall unit 6, fiber optic light cables 7, lighter emitter 8, light detector 10 together form an optical detection assembly. Light from the light emitter 8 is transmitted into the detection volume 5 using a first of the fiber optic cables 7. This first fiber optic cable is consider the emitter optic. Scattered light due to interaction with wax crystals in the detection volume 5 is transmitted by the second fiber optic cable 7 to the light detector 10. This second fiber optic cable is consider the receiver optic. As shown in FIG. 1, light from the light emitter 8 emanates from the side of the detection wall unit 6 into the detection volume 5. The scattered light is collected by the second fiber optic cable 7 located in the detection wall unit 6 at the top of the detection volume 5, as shown in FIG. 1. A data acquisition and control unit 11 is used to collect information from the temperature sensor 4 and the light detector 10, to control the cooling and warming rates of the thermal conductive surface 2 and to analyze the collected data. A microprocessor equipped with the necessary software and hardware is utilized in the data acquisition and control unit 11 for this purpose.

To determine the cloud point, the fuel within the detection volume 5 is cooled quickly by the thermal conductive surface 2, until wax crystals are formed. Thereafter, the fuel is warmed until all wax crystals have melted. Finally, the fuel is cooled once again at a slower rate as dictated by a standard test method established by the American Society of Testing and Materials (ASTM). According to this standard test method, the temperature at which the wax crystals begin to form during this slow-cooling step is defined as the cloud point. The method of the present invention allows a quick determination of cloud point by first scanning a wide temperature region using a fast cooling rate. Once an approximate cloud point is identified under fast cooling, the test is repeated using a slower cooling rate over a much narrower temperature range. However, if one is only interested in an approximate cloud point, then the slow cooling step can be omitted.

Figure 2:
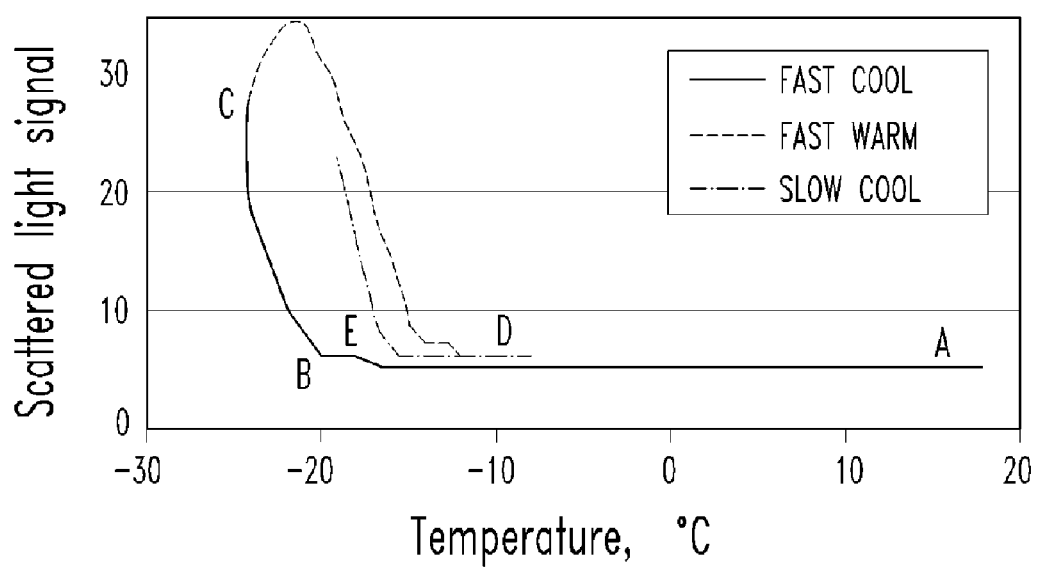
FIG. 2 is a plot showing the determination of cloud point using the cloud point monitoring device of FIG. 1 according to present invention.

As shown in FIG. 1, wax crystal formation 12 within the detection volume 5 will cause light to deviate from a straight path and scatter at different angles, some of which is captured by the fiber optic cable 7 connected to the light detector 10. As a result, the light detector 10 registers an increased level of light. Moreover, the amount of light received can be correlated to the amount of wax crystals being formed. This type of information is useful in itself to monitor the amount of wax buildup in the detection volume 5. FIG. 2 is a graphical plot of results obtained in a typical cloud point test using the cloud point monitoring device of FIG. 1. The test began at A when the sample was at room temperature. The light received by the light detector 10 was at a low level due the lack of scattered light directed towards the second fiber optic cable 7. As the sample was chilled, the light level remained low until wax crystals are formed at B. The formation of wax crystals caused the scattered light level to rise (B to C). Subsequent warming of the sample resulted in melting of the solid phase and a proportional decrease in scattered light (C to D). When all of the wax crystals have melted (D) the sample is once again cooled at a slower rate until wax crystals reappear (D to E). The temperature at which wax crystals reappear (E) is recorded as the cloud point. Since it is important to keep the cloud point monitoring device small, all of the components of the apparatus must be miniaturized. For example, the thermal conductive surface 2 in FIG. 1 measures approximately 1 cm square. A thermally conductive material such as copper or aluminum may be used for the thermal conductive surface 2. It is beneficial to polished thermal conductive surface 2 to a high degree of reflectivity to increase the intensity of scattered light created by the wax crystals. The small thermal mass of the thermal conductive surface 2 permits the use of a small cooler 3. Miniaturized coolers such as Stirling, pulse-tube, or thermoelectric can be used. The miniaturized and lightweight attributes of such coolers make it feasible and convenient to mount inside a fuel tank or fuel line.

Figure 3:
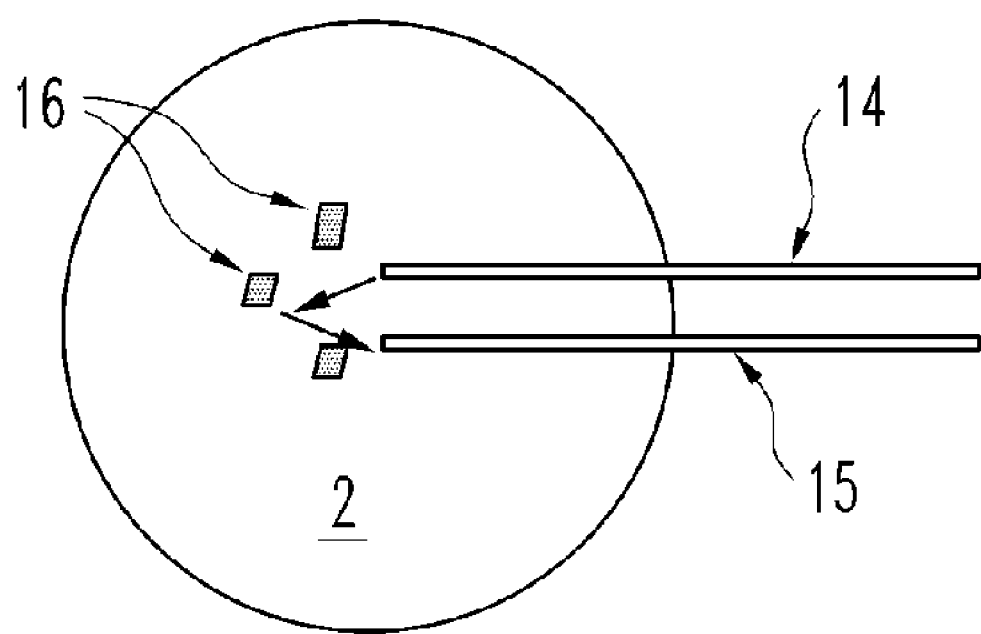
FIG. 3 is a schematic view of another configuration of the cloud point monitoring device according to present invention.
Figure 4:
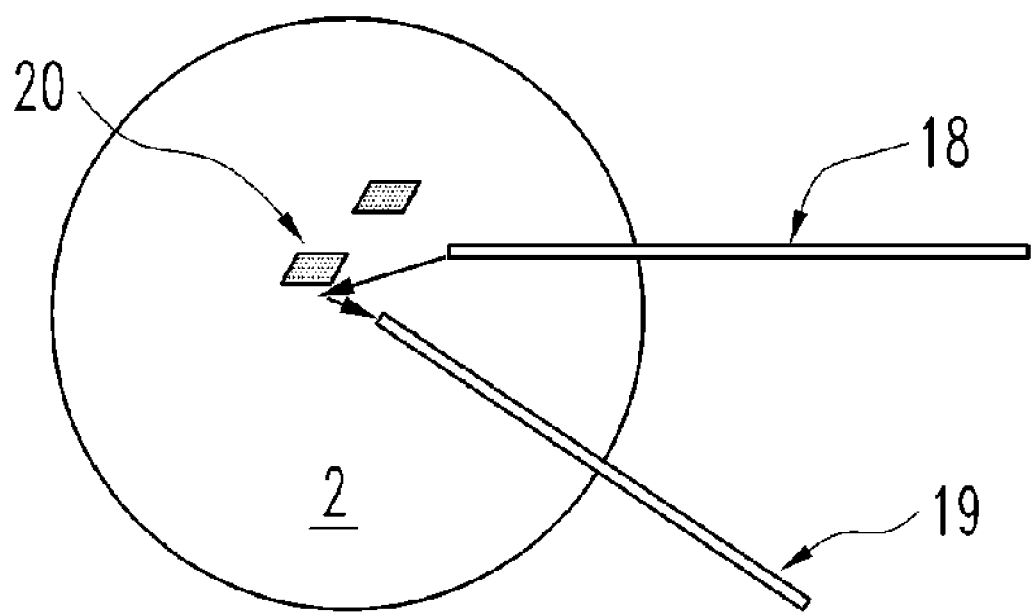
FIG. 4 is a schematic view of another configuration of the cloud point monitoring device according to present invention.
Figure 5:
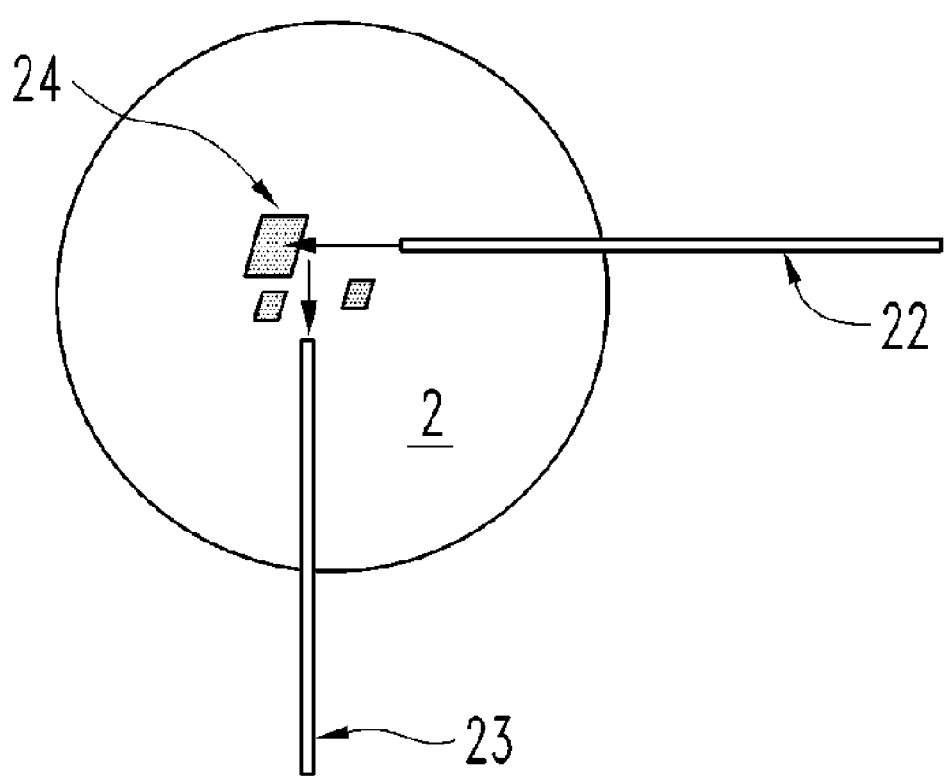
FIG. 5 is a schematic view of another configuration of the cloud point monitoring device according to present invention.
Figure 6:
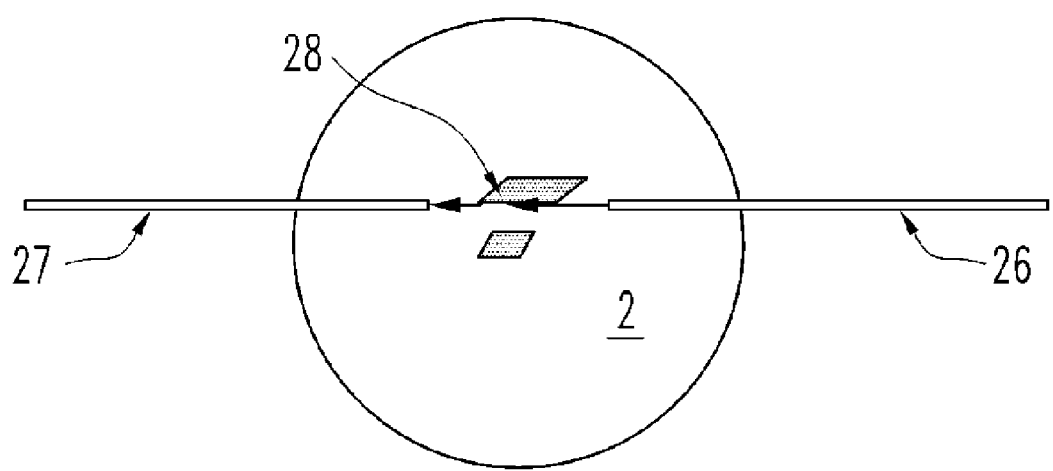
FIG. 6 is a schematic view of another configuration of the cloud point monitoring device according to present invention.
Figure 7:
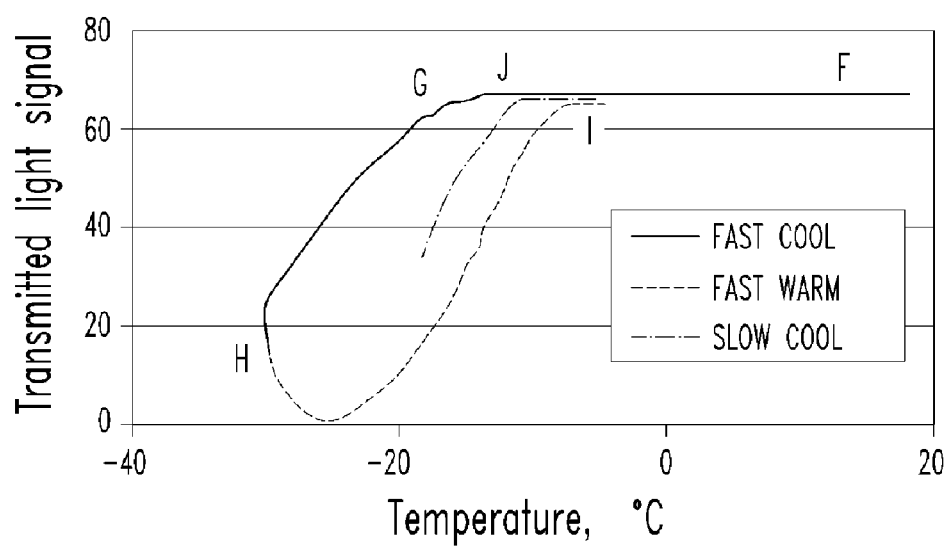
FIG. 7 is a plot showing the determination of cloud point using the cloud point monitoring device of FIG. 6 according to present invention.

FIGS. 3–6 show different variations in which the detection volume 5 is more open and the fiber optic cables are arranged at different angles with respect to one another. For example, FIG. 3 shows a compact arrangement in which two parallel fiber optic cables 14, 15 are placed next to each on top of the thermal conductive surface 2. In this instance, fiber optic cable 14 serves as the emitter optic and fiber optic cable 15 serves as the receiver optic. In this manner, one-hundred-and-eighty degree (180°) backscattered light signal due to wax formation 16 is collected. It is noted that the roles of emitter/receiver optics can be interchanged. The detection wall unit 6 is not shown in FIGS. 3–6, but could be employed. The fiber optic cables in FIGS. 3–6 are positioned on top of the thermal conductive surface 2 or at least very close to the thermal conductive surface 2 to provide improve sensitivity by detecting the wax crystals formed nearest to the thermal conductive surface 2. Whereby, the wax crystals formed nearest to the thermal conductive surface 2 would be the first wax crystals formed and are therefore formed in an area between the emitter optic and the receiving optic, which is considered as the detection volume 5. Similarly, FIG. 4 displays alternative backscatter orientation, FIG. 5 displays ninety degree (90°) side-scatter orientation, and FIG. 6 displays a zero degree (0°) transmission orientation. All of these arrangements make use of two fiber optic cables placed on top of the thermal conductive surface 2, but differ in their relative compactness and detection sensitivity. For example, in FIG. 4, fiber optic cable 18 acts as the emitter optic, while fiber optic cable 19 as the receiver optic receives one-hundred-and-thirty-five degree (135°) backscattered light when wax crystals 20 are formed. In FIG. 5, fiber cable 22 is the emitter optic, while fiber optic cable 23 as the receiver optic receives ninety degree (90°) side-scatter light from wax crystals 24. It noted that the roles of emitter and receiver optics are interchangeable as well. The zero degree (0°) transmission orientation of FIG. 6 is a special case. Rather than observing an increase in light due to light scatter, the amount of light received by the receiver optic would start at a high level due the lack of obstruction along the light path by wax crystals, defined by emitting fiber optic cable 26 and receiving fiber optic cable 27. Whereby, a decrease in the received light levels would result when wax crystals 28 are formed and thereby divert portions of the light beam into other scattering angles. FIG. 7 is a graphical plot of results obtained in a typical cloud point test using the configuration of FIG. 6. The test began at F when the sample was at room temperature. The light received by the light detector 10 was at a high level due complete transmission from the emitting fiber optic cable 26 across into the receiving fiber cable 27. As the sample was chilled, the light level remained high until wax crystals are formed at G. The formation of wax crystals caused light to be scattered away from the receiving fiber cable 27, leading to a decrease of received light level (G to H). Subsequent warming of the sample resulted in melting of the solid phase and an increase in transmitted light (H to I). When all of the wax crystals have melted (I) the sample is slowly cooled until wax crystals reappear (I to J). The temperature at which wax crystals reappear (J) is recorded as the cloud point.

Figure 8:
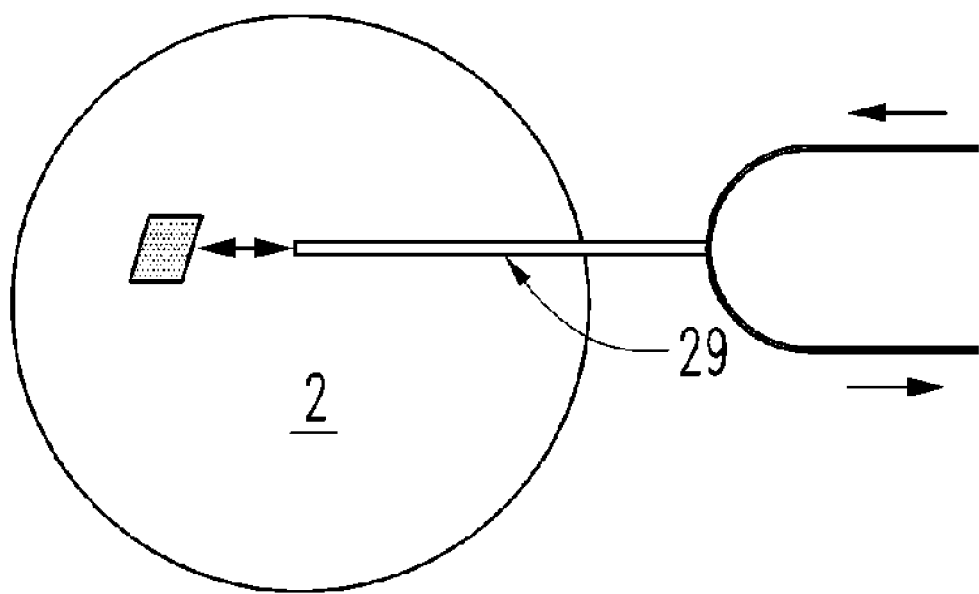
FIG. 8 is a schematic view of another configuration of the cloud point monitoring device according to present invention.
Figure 9:
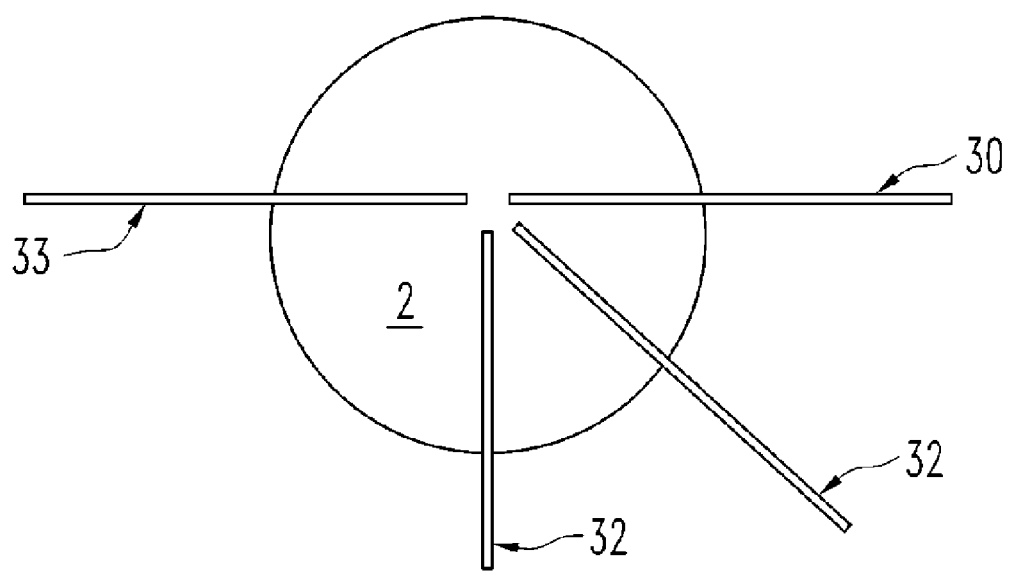
FIG. 9 is a schematic view of another configuration of the cloud point monitoring device according to present invention.
Figure 10:
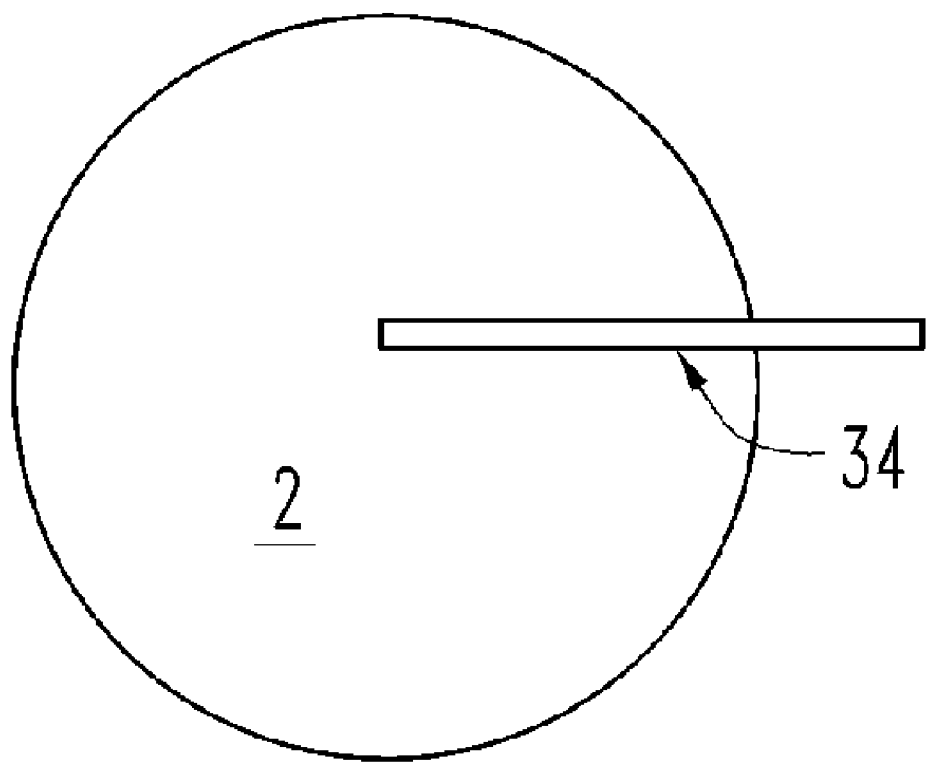
FIG. 10 is a schematic view of another configuration of the cloud point monitoring device according to present invention.
Figure 11:
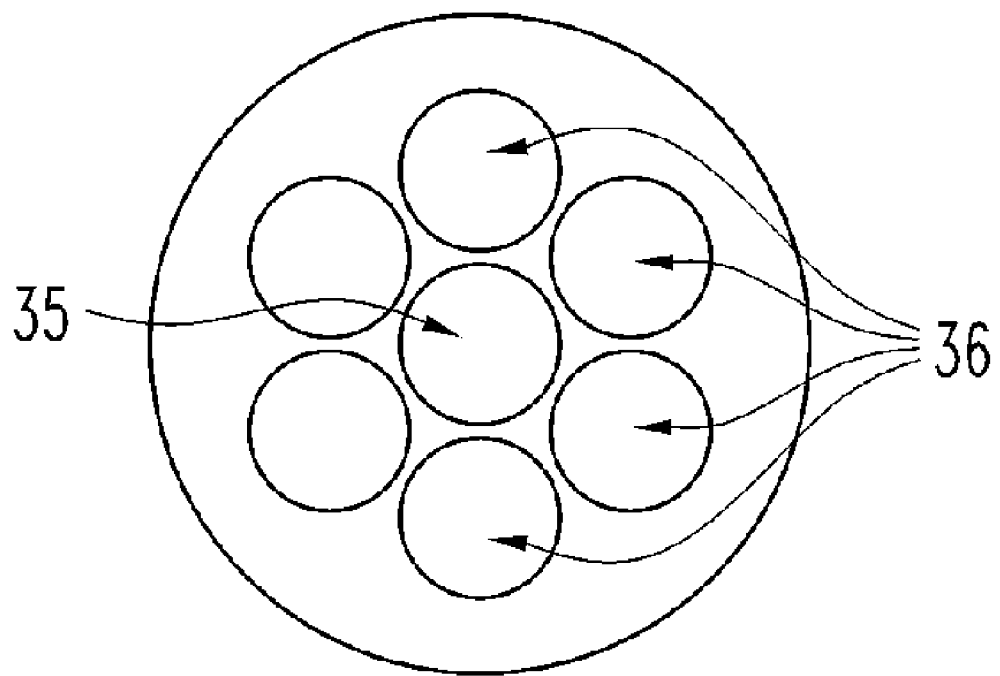
FIG. 11 is a cross-sectional view of a bundle of fiber optic cables shown in FIG. 10 according to the present invention.

The number of emitting and receiving fiber optic cables is not limited to one of each kind. FIG. 8 illustrates a known fiber optic cable pigtail configuration in which a single fiber optic cable 29 is introduced into the fuel. The fiber optic cable 29 functions both as a light emitter and receiver using the pigtail illustrated outside of the fuel source. This is an extremely compact way of detecting one-hundred-and-eighty degree (180°) backscattered light. In contrast, multiple fibers can serve as emitters and receivers of light, adding redundancy and multiple-angle detection flexibility to the system, as well as enhancing signal output. As illustrated in FIG. 9, any of the fiber optic cables 30, 31, 32, and 33 can serve as the emitter optics, while the remaining fiber optic cables that are not used as emitter optics can serve as receiver optics. In particular, a cable of multiple optic fibers bundled together can also be used. For example, FIG. 10 illustrates the case where a fiber bundle 34 is introduced into the fuel. FIG. 11 shows a cross-sectional view of the fiber bundle 34 in which the center fiber 35 of the bundle acts as the light emitter, while the surrounding fibers 36 function as receivers.

Figure 12:
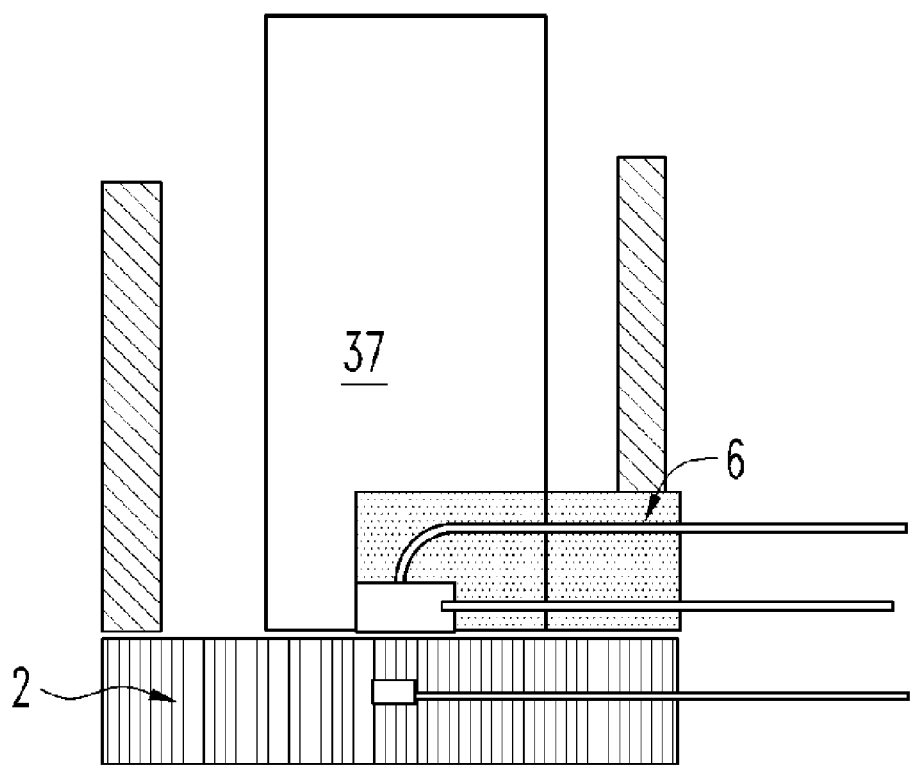
FIG. 12 is a schematic view of another configuration of the cloud point monitoring device according to present invention.
Figure 13:
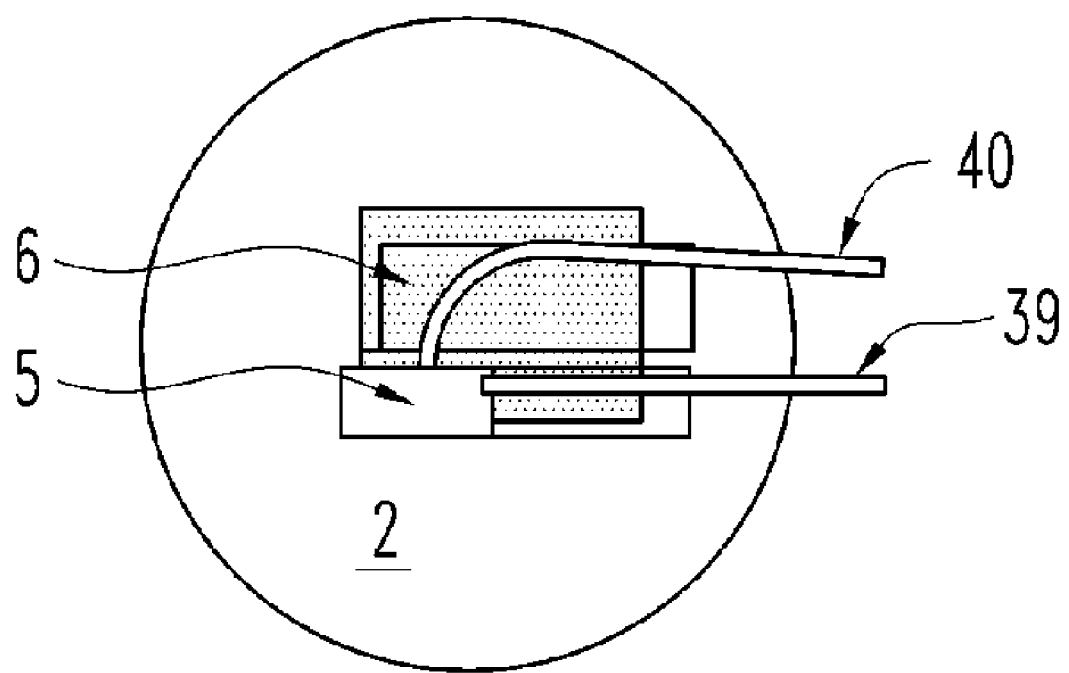
FIG. 13 is a schematic view of another configuration of the cloud point monitoring device according to present invention.
Figure 14:
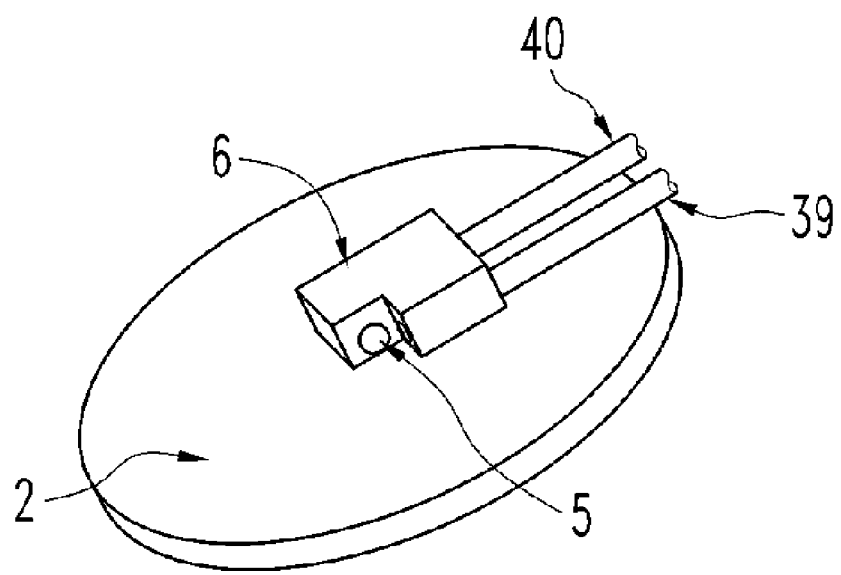
FIG. 14 is a perspective view of the configuration shown in FIG. 13 according to the present invention.
Figure 15:
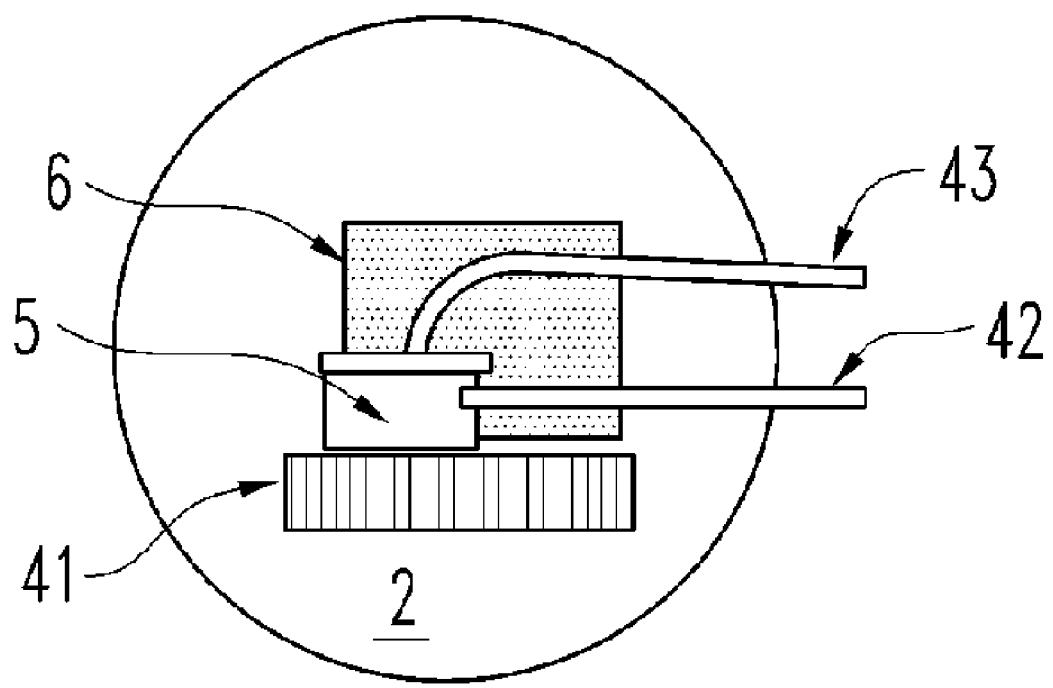
FIG. 15 is a schematic view of another configuration of the cloud point monitoring device according to present invention.
Figure 16:
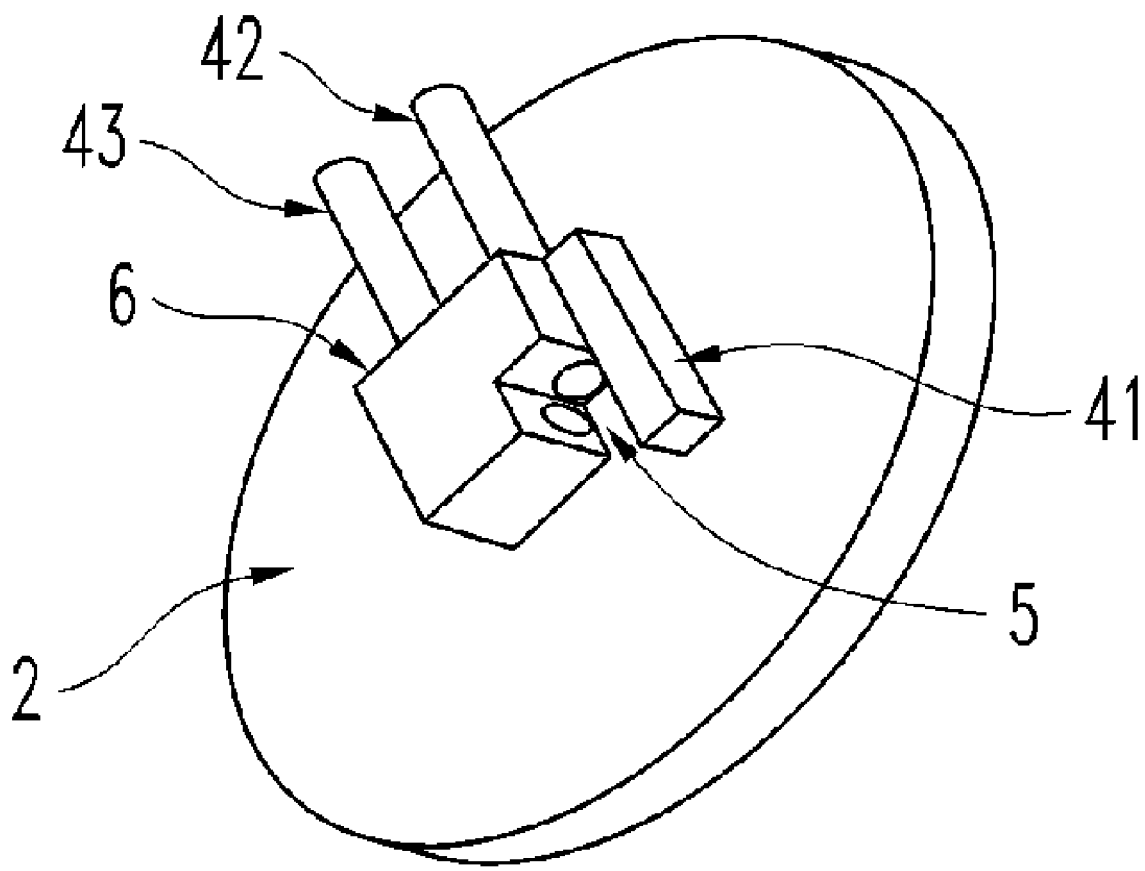
FIG. 16 is a perspective view of the configuration shown in FIG. 15 according to the present invention.
Figure 17:
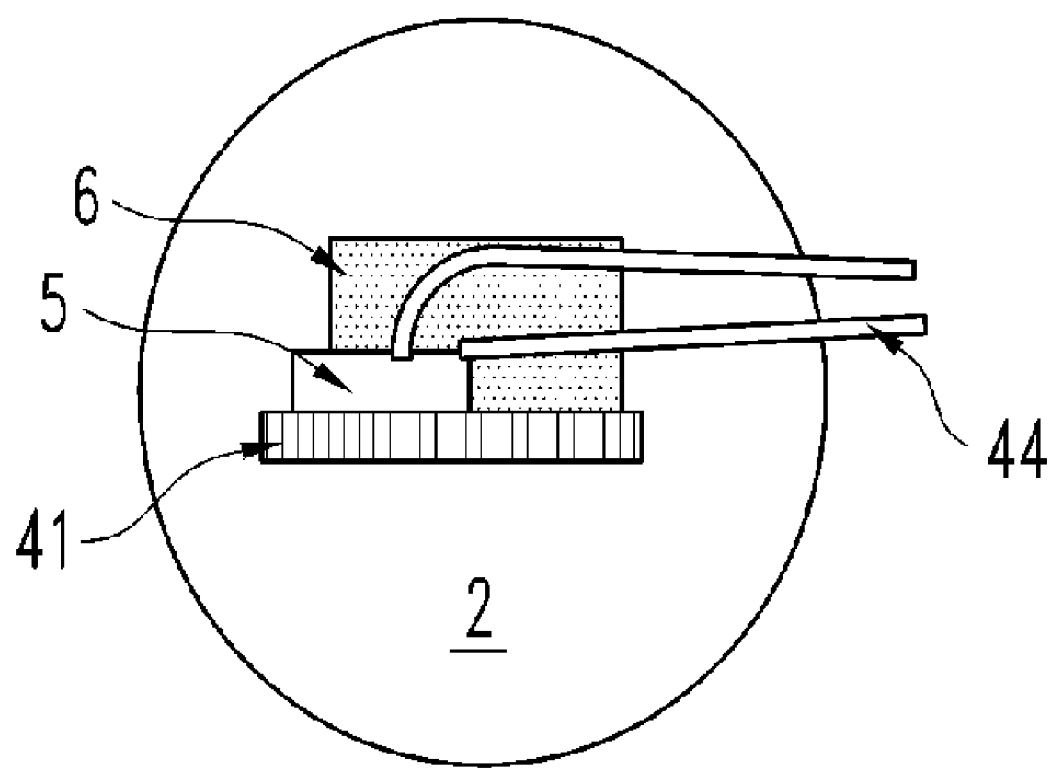
FIG. 17 is a schematic view of another configuration of the cloud point monitoring device according to present invention.
Figure 18:
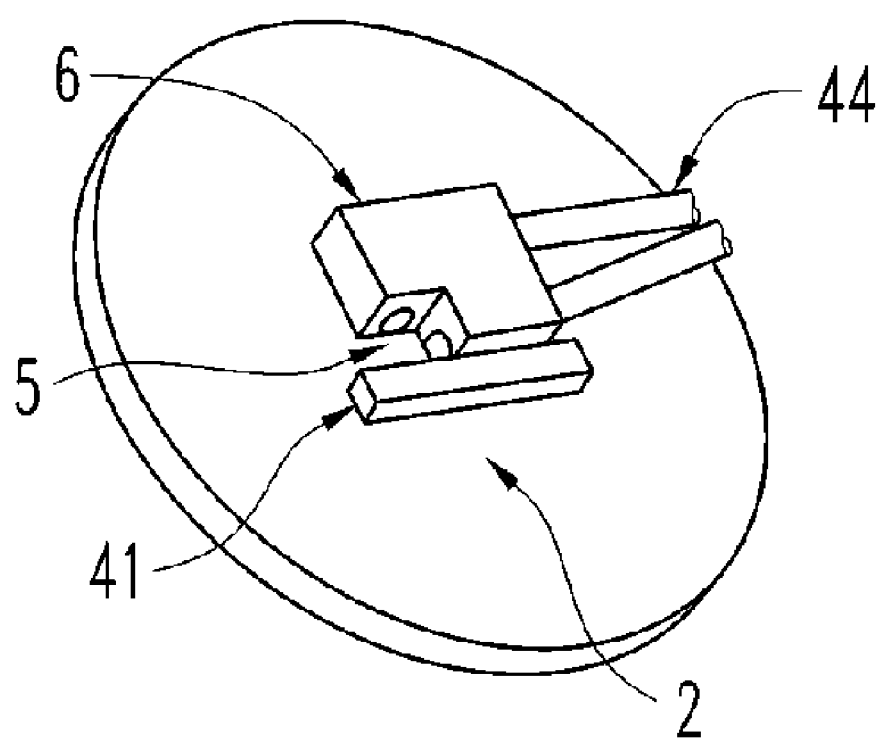
FIG. 18 is a perspective view of the configuration shown in FIG. 17 according to the present invention.

Returning to the configuration of FIG. 1, further enhancements can be made to improve other aspects. For example, to maximize cooling efficiency and maintain localized cooling within the detection volume 5, it is beneficial to minimize turbulence and convective flow of fuel in and out of the detection volume 5 during cloud point testing. To minimize turbulence and convective flow of fuel, the cloud point monitoring device can be sheltered by side walls 37 to shield the fuel in the detection volume 5 from large-scale movement of the fuel surrounding the detection volume 5, as shown in FIG. 12. The walls 37 could be constructed to be continuous and meet at the top (not shown) to further shield the detection volume 5. In cases where the flow of fuel becomes too restrictive to place the cloud point monitoring device within the confines of the walls 37, an alternative is to turn the detection wall unit 6 on its side, as shown in FIGS. 13 and 14. As a result, the detection volume 5 is bounded on two consecutive sides by the detection wall unit 6, whereby the detection wall unit 6 protects the detection volume 5 from the effects of the flow of fuel. The top and remaining two sides are open to the fuel to fill the detection volume 5. In this manner, the change-out of fuel in the detection volume 5 is somewhat protected from large-scale movement of the fuel surrounding the detection volume 5,. To provide further enhancement of the detection volume 5 of the configuration shown in FIGS. 13–14, an additional thermal conductive sidewall surface 41 can be erected as part of the thermal conductive surface 2, as shown in FIGS. 15–16. In this manner, the detection volume 5 will be bounded below and on one side by thermal conductive surfaces 2, 41. The additional thermal conductive sidewall surface 41 serves as an additional wax crystal growth site to congregate more wax crystals into the detection volume 5, thus improving detection sensitivity. Finally, even greater sensitivity can be gained by orienting the emitting fiber optic cable 44 towards the side cold surface 41, as shown in FIGS. 17–18, hence directing a greater portion of light into an area with a high concentration of wax crystals. By so doing, the scattering efficiency is improved, leading to greater amount of scattered light to be received. This can be done in all disclosed configurations of the cloud point monitoring device, whereby placing the emitter optic as close as possible to the thermal conductive surface 2 will increase sensitivity of the cloud point monitoring device.

Figure 19:
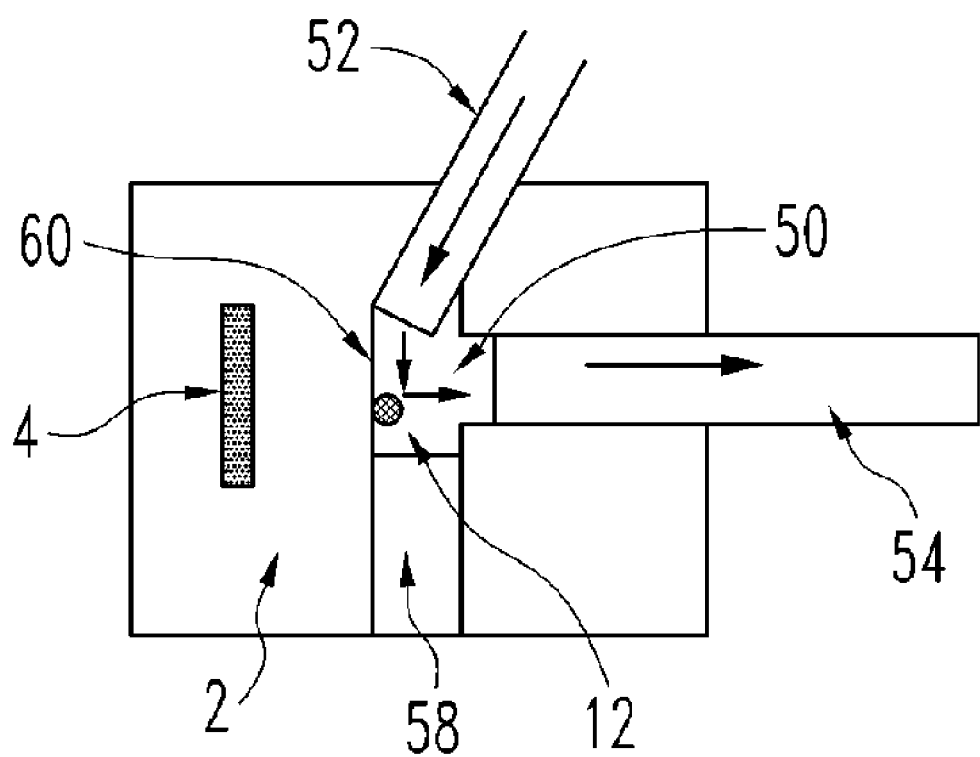
FIG. 19 is a schematic view of another configuration of the cloud point monitoring device according to present invention.
Figure 20:
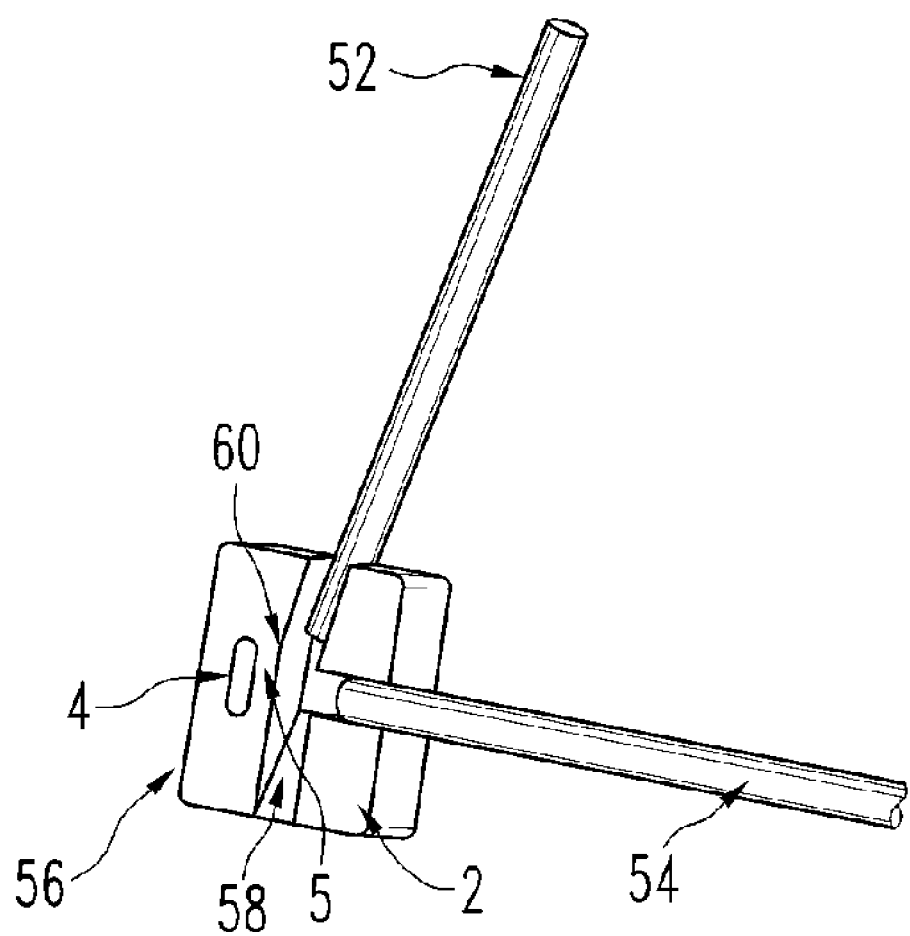
FIG. 20 is a perspective view of the configuration shown in FIG. 19 according to the present invention.

FIGS. 19–20 show a combination of some of the enhancements discussed above which are incorporated into a single cloud point monitoring device. The thermal conductive surface 2 is shown as a small plate which acts as the main body of cloud point monitoring device. The thermal conductive surface 2 includes two channels 50 which lead into the detection volume 5. In one channel 50 is a light emitting fiber optic cable 52 and in the other channel 50 is the light detecting fiber optic cable 54. The detection volume 5 in this configuration is an open area embedded below an upper surface 56 of the thermal conductive surface 2 and between the fiber optic channels 50. The temperature sensor 4 is shown embedded into the thermal conductive surface 2. The thermal conductive surface 2 includes a ramp 58 which leads from the upper surface 56 of the thermal conductive surface 2 on down to the detection volume 5. The use of the ramp 58 encourages more wax crystals 12 to gather into the detection volume 5, thus increasing the probability of light scattering and increasing the sensitivity of the cloud point monitoring device. The ramp 58 provides the most improved sensitivity, if positioned opposite the emitting fiber optic cable 52. The emitting fiber optic cable 52 is preferentially tilted to direct light partially onto an optically reflexive side surface 60, as shown in FIGS. 19–20. Tilting the light towards the reflexive side surface 60 has the effect of enhancing the amount of light scattered by crystals 12. It should be noted that the emitting fiber optic cable 52 should not be tilted so that light is directly reflected into the detecting fiber optic cable 54, if the method of detecting increased light levels due to crystal formation is utilized. As discussed before, the cooler 3 can be integral to the thermal conductive surface 2 or attached to the thermal conductive surface 2. This configuration of the cloud point monitoring device provides the simplest version to manufacture, fewest parts and simplifies installation in a fuel system due its simplicity, yet provide improved sensitivity. This configuration can be placed directly into a fuel system or installed within the side walls 37 shown in FIG. 12.

Figure 21:
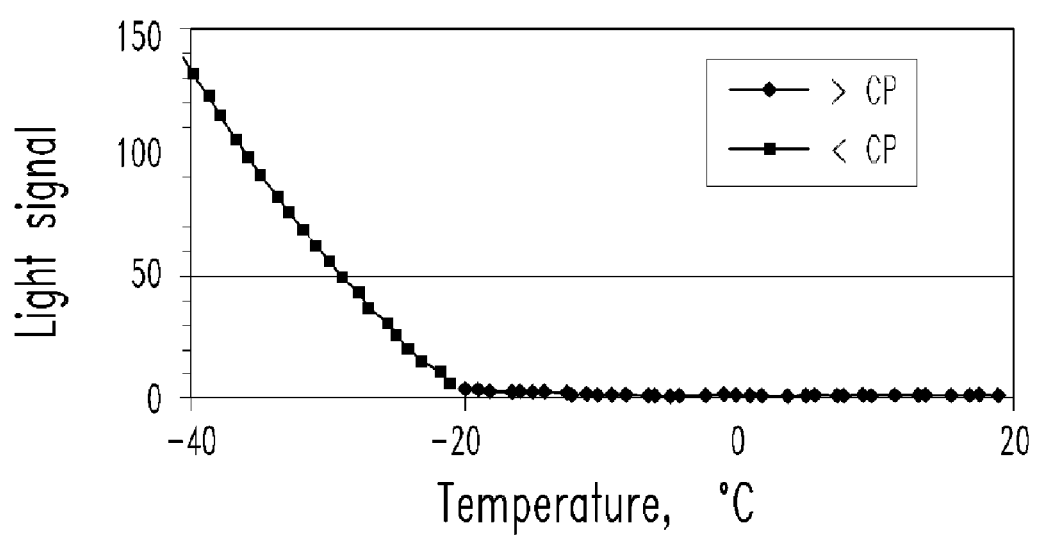
FIG. 21 is a plot showing the experimental record of light intensity and temperature of a diesel fuel above and below its cloud point according to the present invention.

Other more qualitative information may be obtained from using the cloud point monitoring device to determine the cloud point of diesel fuel. The types of information include the extent of wax buildup as well as an approximate indication of the energy content of the fuel. Both are of value to operators of diesel engines. It has been verified through microscopic particle counting that as the fuel temperature decreases below the cloud point, the number of wax particles in the detection volume 5 of the cloud point monitoring of FIG. 1 increases proportionately. Simultaneously, the amount of scattered light also increases. For example, FIG. 21 plots the temperature of a diesel fuel tested by the cloud point monitoring device versus the scattered light level. Therefore, the amount of scattered light due to wax crystal formation is directly related to the amount of wax buildup. Although this relationship can be quantified more exactly using other means of measurement, it is not necessarily the primary interest of the operators, who are often interested in a more practical index of crystallization instead of an exact quantification of wax content in weight or volume percent. Nevertheless, it remains true that the above relation between scattered light and wax buildup can be approximately qualified using the cloud point monitoring device. For example, in the absence of cooling the thermal conductive surface 2, the other components of the optical detection assembly alone enable the detection and monitoring of the buildup of wax as fuel is subjected to changes in ambient temperatures. Descriptive terms such as "no wax buildup", "minor wax buildup" or "intense wax buildup" may be applied to characterize the condition of wax formation in the detection volume 5, and by extension, to that of the fuel in general. Therefore, a secondary function of this invention is that of a qualitative wax monitor, which can be utilized with or without the thermal conductive surface 2.

Figure 22:
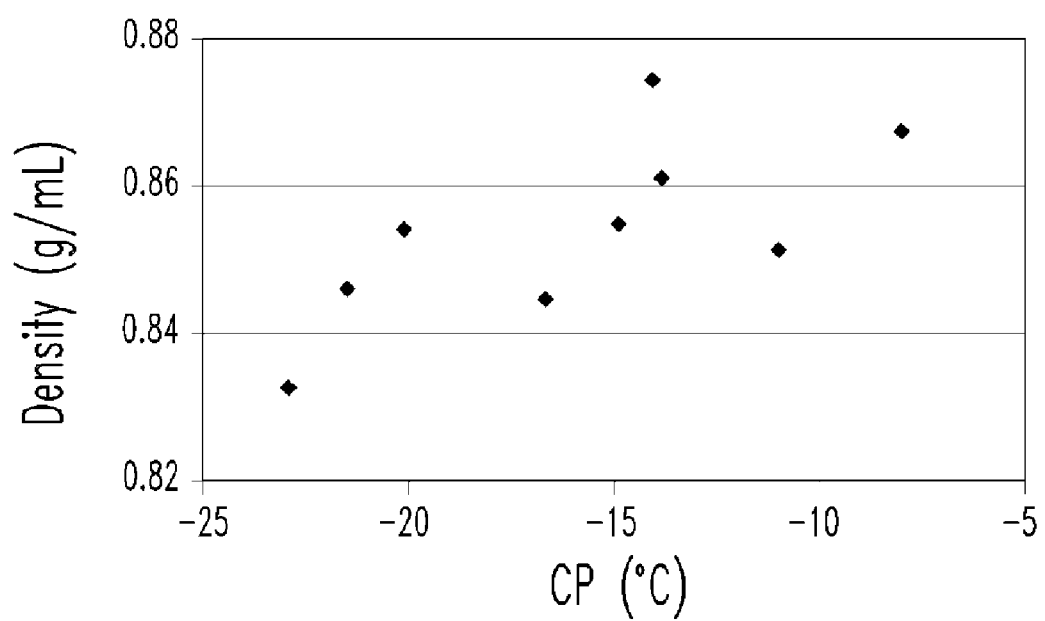
FIG. 22 is a plot showing a correlated relation between cloud point and fuel density according to the present invention.
Figure 23:
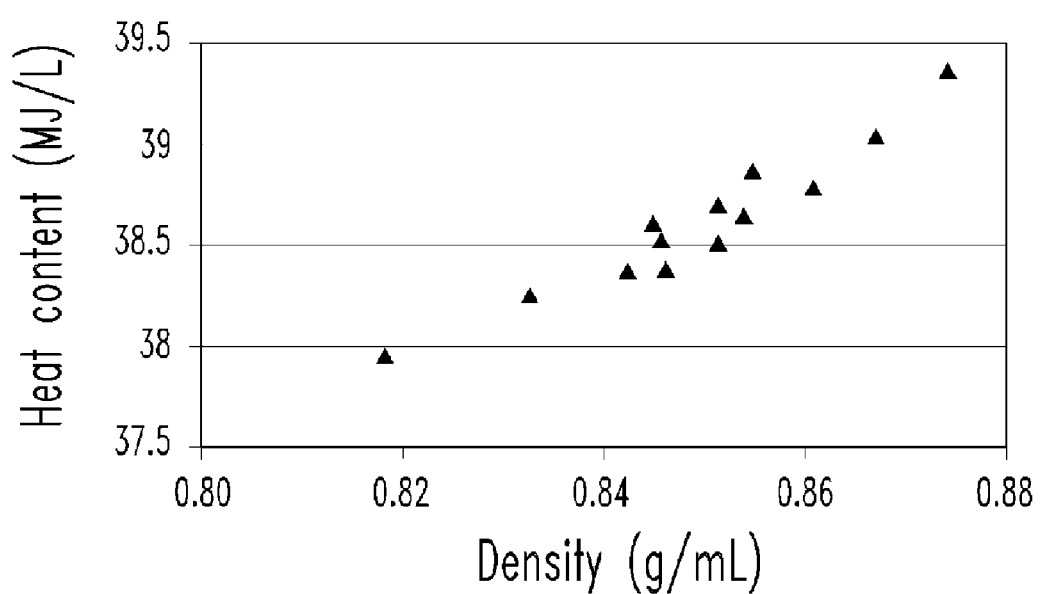
FIG. 23 is a plot showing a correlated relation between energy content and fuel density according to the present invention.

The approximate energy content of the fuel is yet another piece of useful information that can be deduced from the cloud point monitoring device. Empirically, it has be determined that an approximate linear function relating the cloud point of a diesel fuel to its energy content via the fuel density. According to this relationship, the higher the cloud point, the greater the energy content. FIGS. 22 and 23 illustrate the correlation between density and cloud point of a variety of diesel fuels, and between density and energy content respectively. As a result, this invention serves a tertiary role as an approximate energy content indicator. Accordingly, descriptive terms such as "low", "medium" or "high" can be used to qualify the energy content of the fuel, based on the determined cloud point of the fuel to be used.

While different embodiments of the invention have been described in detail herein, it will be appreciated by those skilled in the art that various modifications and alternatives to the embodiments could be developed in light of the overall teachings of the disclosure. Accordingly, the particular arrangements are illustrative only and are not limiting as to the scope of the invention that is to be given the full breadth of any and all equivalents thereof.

What is claimed is:

1. A cloud point monitoring device for installation in a fuel flow system of a vehicle, for determining formation of wax crystals in diesel fuel in the vehicle, comprising:
   a thermal conductive surface;
   a thermal device to change thermal conditions of said thermal conductive surface;
   a detection volume in close proximity to said thermal conductive surface, said detection volume being open to the fuel flow system of the vehicle to allow fuel to flow through said detection volume;
   a temperature sensor to sense temperature of the diesel fuel in said detection volume;
   a light source which produces and directs light into said detection volume;
   a light detector to detect a change in light level from said light source in said detection volume, said change in light level being relative to the positioning of said light source in relation to said light detector; and
   a data acquisition and control unit to monitor light level from said light detector and monitor diesel fuel temperature from said temperature sensor.

2. The cloud point monitoring device of claim 1, wherein said detection volume is an open area embedded inside said thermal conductive surface.

3. The cloud point monitoring device of claim 2, wherein said thermal conductive surface includes a channel within said thermal conductive surface to direct the light from said light source into said embedded detection volume and wherein said thermal conductive surface includes a channel within said thermal conductive surface to said light detector in order to detect the change in light level from said light source that has been directed into said embedded detection volume.

4. The cloud point monitoring device of claim 3, wherein a fiber optic cable directs the light from said light source into said detection volume along said channel and wherein a fiber optic cable detects the change in light from said light source that has been directed into said embedded detection volume and transmits the light to said light detector along said channel.

5. The cloud point monitoring device of claim 2, wherein said detection volume includes a reflective side surface to enhance scattering of the light towards said light detector.

6. The cloud point monitoring device of claim 5, wherein said light source is directed towards said reflective side surface, so that the light is directed towards said reflective side surface.

7. The cloud point monitoring device of claim 2, wherein said thermal device is embedded in said thermal conductive surface.

8. The cloud point monitoring device of claim 2, wherein said thermal device is a cooler.

9. The cloud point monitoring device of claim 8, wherein said cooler is embedded in said thermal conductive surface.

10. The cloud point monitoring device of claim 1, wherein said temperature sensor is embedded in said thermal conductive surface.

11. The cloud point monitoring device of claim 2, wherein said temperature sensor is embedded in said thermal conductive surface.

12. The cloud point monitoring device of claim 1, wherein said detection volume is formed by a detection wall unit above said thermal conductive surface.

13. The cloud point monitoring device of claim 12, wherein said detection wall unit emanates from said thermal conductive surface.

14. The cloud point monitoring device of claim 12, wherein said light source emanates from said detection wall unit into said detection volume and wherein said light detector includes a light transmitting device in said detection wall unit to detect changes in said light level in said detection volume.

15. The cloud point monitoring device of claim 14, wherein said light source includes a fiber optic cable which emanates from said detection wall unit and wherein said light transmitting device of said light detector is a fiber optic cable.

16. The cloud point monitoring device of claim 12, wherein said cloud point monitoring device is positioned between two walls to protect said cloud point monitoring device from random movement of the diesel fuel, yet allow fuel to pass through said cloud point monitoring device.

17. The cloud point monitoring device of claim 1, wherein said light source is positioned relative to said light detector, such that there is an increase in said light level due to the formation of said wax crystals, whereby the formation of said wax crystals scatters said light towards said light detector.

18. The cloud point monitoring device of claim 1, wherein said light source is positioned relative to said light detector, such that there is a decrease in said light level due to the formation of said wax crystals, whereby the formation of said wax crystals blocks said light away from said light detector.

19. The cloud point monitoring device of claim 2, wherein said light source is positioned relative to said light detector, such that there is an increase in said light level due to the formation of said wax crystals, whereby the formation of said wax crystals scatters said light towards said light detector.

20. The cloud point monitoring device of claim 2, wherein said light source is positioned relative to said light detector, such that there is a decrease in said light level due to the formation of said wax crystals, whereby the formation of said wax crystals blocks said light away from said light detector.

21. The cloud point monitoring device of claim 5, wherein said light source is positioned relative to said light detector, such that there is an increase in said light level due to the formation of said wax crystals, whereby the formation of said wax crystals scatters said light towards said light detector.

22. The cloud point monitoring device of claim 12, wherein said light source is positioned relative to said light detector, such that there is an increase in said light level due to the formation of said wax crystals, whereby the formation of said wax crystals scatters said light towards said light detector.

23. The cloud point monitoring device of claim 12, wherein said light source is positioned relative to said light detector, such that there is a decrease in said light level due to the formation of said wax crystals, whereby the formation of said wax crystals blocks said light away from said light detector.

24. The cloud point monitoring device of claim 1, wherein a surface of said thermal conductive surface near said detection volume is reflective to reflect light and enhance the scattering of light towards said light detector.

25. The cloud point monitoring device of claim 1, wherein said light source and light detector are mounted very near said thermal conductive surface such that the first wax crystals formed nearest to said thermal conductive surface are detected in said detection volume and wherein said light source and light detector are positioned so that a minimal amount of light from said light source is detected by said light detector when there are no wax crystals in the fuel.

26. The cloud point monitoring device of claim 1, wherein said light source and light detector are mounted very near said thermal conductive surface such that crystals formed first nearest to said thermal conductive surface are detected in said detection volume and wherein said light source and light detector are positioned so that all of the light from said light source is detected by said light detector when there are no wax crystals in the fuel.

27. A cloud point monitoring device, for determining formation of wax crystals in diesel fuel, comprising:
a thermal conductive surface;
a thermal device to change thermal conditions of said thermal conductive surface;
a detection volume in close proximity to said thermal conductive surface;
a temperature sensor to sense temperature of the diesel fuel in said detection volume;
a light source which directs light into said detection volume;
a light detector to detect a change in light level from said light source in said detection volume, said change in light level being relative to the positioning of said light source in relation to said light detector;
a data acquisition and control unit to monitor light level from said light detector and monitor diesel fuel temperature from said temperature sensor; and
a ramp in said detection volume which leads from an upper surface of said thermal conductive surface down to a bottom of said detection volume.

28. A method of monitoring cloud point of diesel fuel in a veicle, using a cloud point monitoring device which includes a thermal conductive surface, a thermal device to change thermal conditions of the thermal conductive surface, a detection volume in close proximity to the thermal conductive surface, a temperature sensor to sense temperature of the diesel fuel in the detection volume; a light source which directs light into the detection volume, a light detector to detect a change in light level from the light source in the detection volume, the change in light level being relative to the positioning of the light source in relation to the light detector, and a data acquisition and control unit to monitor light level change from the light detector and monitor diesel fuel temperature from the temperature sensor, comprising:
inputting fuel into the detection volume from a fuel flow system of the vehicle;
directing light from the light source into the detection volume;
detecting the light level at the light detector
monitoring the light level change at the light detector;

sensing and monitoring the temperature of the diesel fuel in the detection volume;

cooling the diesel fuel in detection volume until wax crystals are formed, so that the light level monitored is changed; and recording temperature of the diesel fuel in the detection volume at a value point where the light level changes, the recorded temperature at the value point where the light level changes being the cloud point of the diesel fuel.

29. The method of claim 28, wherein the detection volume has an open area embedded inside the thermal conductive surface.

30. The method of claim 28, wherein the detection volume is formed by a detection wall unit above the thermal conductive surface.

31. The method of claim 28, further including performing the cooling in the detection volume at a rapid pace so that the recorded temperature is a first sensed temperature that is a recorded approximate of the cloud point and considered in the region of the cloud point of the fuel.

32. The method of claim 31, wherein temperature of the recorded approximate of the cloud point is a first temperature point; further warming the diesel fuel slightly above the first temperature point to dissipate the wax crystals formed; further cooling the diesel fuel at a slower rate in the detection volume until wax crystals are formed, so that the light level monitored is changed; and recording a second temperature point where the light level change was detected at the slower rate of cooling, the second temperature being an accurate determination of the cloud point of the diesel fuel.

33. The method of claim 28, further including using the data acquisition and control unit to correlate the recorded cloud point temperature with a current temperature of the diesel fuel colder than the cloud point to determine an approximate amount of wax crystal build up in the diesel fuel based on know relationships between wax content and temperature below the cloud point.

34. The method of claim 28, further including using the data acquisition and control unit to correlate the cloud point of the diesel fuel in order to approximate energy content of the diesel fuel based on a known relationship of energy content of diesel fuel to cloud point value.

35. The cloud point monitoring device of claim 28, wherein the light source and light detector are mounted very near the thermal conductive surface such that the first wax crystals formed nearest to the thermal conductive surface are detected in the detection volume and wherein the light source and light detector are positioned so that a minimal amount of light from the light source is detected by the light detector when there are no wax crystals in the fuel.

36. The cloud point monitoring device of claim 28, wherein the light source and light detector are mounted very near the thermal conductive surface such that the crystals formed first nearest to the thermal conductive surface are detected in the detection volume and wherein the light source and light detector are positioned so that all of the light from the light source is detected by the light detector when there are no wax crystals in the fuel.

* * * * *